United States Patent [19]
Wohlfarth et al.

[11] 4,102,860
[45] Jul. 25, 1978

[54] SILICON-TIN COMPOUNDS AS CONDENSATION CATALYSTS IN THE PREPARATION OF ORGANOPOLYSILOXANE ELASTOMERS

[75] Inventors: Ernst Wohlfarth; Wolfgang Hechtl; Paul Hittmair, all of Burghausen, Germany

[73] Assignee: Wacker-Chemie GmbH, Munich, Germany

[21] Appl. No.: 755,532

[22] Filed: Dec. 30, 1976

Related U.S. Application Data

[62] Division of Ser. No. 690,683, May 27, 1976.

[30] Foreign Application Priority Data

May 30, 1975 [DE] Fed. Rep. of Germany ....... 2524000

[51] Int. Cl.$^2$ ............................................ C08G 77/04
[52] U.S. Cl. ..................................... 528/18; 260/18 S; 260/29.1 SB; 260/31.6; 260/37 SB; 260/429.7; 260/827; 528/35; 528/34; 528/30; 528/9

[58] Field of Search ......................... 260/46.5 G, 18 S

[56] References Cited

U.S. PATENT DOCUMENTS

| 2,843,555 | 7/1958 | Berridge | 260/46.5 G |
| 3,186,963 | 6/1965 | Lewis et al. | 260/46.5 Y |
| 3,560,244 | 2/1971 | Neuroth | 260/46.5 G |
| 3,678,002 | 7/1972 | Nitzsche et al. | 260/46.5 G |
| 3,810,925 | 5/1974 | Viksne | 260/46.5 G |

Primary Examiner—Melvyn I. Marquis

[57] ABSTRACT

Silicon-tin compounds of the formula

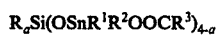

$$R_a Si(OSnR^1R^2OOCR^3)_{4-a}$$

in which R represents an alkyl or phenyl radical, $R^1$, $R^2$ and $R^3$ are alkyl radicals and $a$ is 0 or 1 and there use as condensation catalysts in the preparation of organopolysiloxane elastomers.

8 Claims, No Drawings

SILICON-TIN COMPOUNDS AS CONDENSATION CATALYSTS IN THE PREPARATION OF ORGANOPOLYSILOXANE ELASTOMERS

This is a division of application Ser. No. 690,683, filed May 27, 1976.

The present invention relates to silicon-tin compounds, particularly to a method for preparing the same, and to their use as condensation catalysts in the preparation of organopolysiloxane elastomers.

Certain silicon-tin compounds have been described heretofore as condensation catalysts in the preparation of organopolysiloxane elastomers (cf., for example, German Democratic Republic Patent Specification No. 83248). However, these silicon-tin compounds are liquid at room temperature.

Therefore it is an object of this invention to prepare silicon-tin compounds which are crystalline at room temperature. Another object of this invention is to provide silicon-tin compounds which may be used as condensation catalysts. A further object of this invention is to provide silicon-tin compounds which may be used in the preparation of organopolysiloxane elastomers.

The foregoing objects and other which will become apparent from the following description are accomplished in accordance with this invention, generally speaking, by providing a compound of the general formula $$R_aSi(OSnR^1R^2OOCR^3)_{4-a}$$

in which R represents an alkyl or phenyl radical, $R^1$, $R^2$ and $R^3$, which may be the same or different, represent alkyl radicals, and $a$ is 0 or 1.

These compounds have certain advantages over the silicon-tin compounds used heretofore. For example, they are crystalline even at room temperature. Also they contain less tin per molecule than do the above mentioned silicon-tin compounds; however, they are just as effective as condensation catalysts as the silicon-tin compounds used heretofore.

The alkyl radical represented by R preferably contains up to 4 carbon atoms, for example, a methyl, ethyl, n-propyl, isopropyl, n-butyl or sec-butyl radical. It is preferably a methyl radical since this is more readily available.

Each alkyl radical represented by $R^1$ or $R^2$ preferably contains up to 18 carbon atoms, such as for example, methyl, ethyl, n-propyl, isopropyl, n-butyl, sec-butyl, n-hexyl, sec-hexyl, n-heptyl, sec-heptyl, n-octyl, 2-ethylhexyl, n-decyl, n-dodecyl, n-tetradecyl or n-octadecyl radical. The methyl, n-butyl, n-octyl and 2-ethylhexyl radicals are preferred as these are more readily available. It is also preferred that all the radicals represented by $R^1$ and $R^2$ be identical, since the starting materials are more readily available.

The alkyl radicals represented by $R^3$ preferably contains up to 4 carbon atoms. Examples of suitable alkyl radicals represented by $R^3$ are methyl, ethyl, propyl, n-butyl and sec-butyl radicals. Again, the methyl radical is preferred, not only because it is more readily available, but also because the ester formed as a by-product during the preparation of the compound of this invention is then an acetate, which can be readily removed by distillation.

The silicon-tin compounds of this invention may be prepared by reacting a silane of the general formula $$R_aSi(OR^4)_{4-a}$$

with a dialkyltin salt of the general formula $$R^1R^2Sn(OOCR^3)_2$$

in which $R^4$ represents a monovalent hydrocarbon radical having up to 4 carbon atoms and R, $R^1$, $R^2$, $R^3$ and $a$ are the same as above, in a molar ratio of (4-a) moles of dialkyltin salt per mole of silane, at a temperature in the range of from 50° to 160° C, while removing as a by-product an ester of the general formula $$R^3COOR^4$$

in which $R^3$ and $R^4$ are the same as above, until the amount of ester that has been removed is within the range of from 80 to 100 percent of the amount theoretically formed by complete reaction of the silane with the dialkyltin salt.

Generally, when one polyfunctional compound reacts with another polyfunctional compound a number of reaction products are theoretically possible, although some of these may be formed only in small amounts. In particular, a product containing only one radical derived from the first polyfunctional compound and, for example, only three radicals derived from the second polyfunctional compound, and containing a further functional group is not normally obtained in an appreciable yield. Even when a polyfunctional compound reacts with a monofunctional compound, generally only those compounds can be isolated in which all functional groups are substituted by the groups derived from the monofunctional compound. (This is illustrated by the list of stannosiloxanes in W. Noll, *Chemie und Technologie der Silicone*, 2nd edition, Weinhaim 1968, p. 296). It is, therefore, particularly surprising that a compound of the invention is formed from the above reaction with a trifunctional or tetrafunctional silane and a difunctional dialkyltin diacylate.

The nature of the hydrocarbon radicals represented by $R^4$, and whether these radicals are the same or different, is of little consequence since these radicals are not present in the compound of this invention. Preferably, however, each $R^4$ represents a methyl or ethyl radical since these are more readily available. In addition, $R^4$ may also represent, for example, another alkyl radical, e.g., an n-propyl, isopropyl, n-butyl or sec-butyl radical, or an alkenyl radical, e.g., a vinyl, allyl or isopropenyl radical.

Examples of silanes represented by the above general formula are tetramethyl silicate, tetraethyl silicate, tetra-n-propyl silicate, methyltriethoxysilane, n-propyltrimethoxysilane, n-propyltriethoxysilane, and phenyltriethoxysilane.

Examples of dialkyltin salts represented by the above general formula are di-n-butyltin diacetate, di-n-octyltin diacetate and di-n-butyltin di-n-propionate.

The reaction is preferably carried out at atmospheric pressure, namely at or about 760 torr, e.g., 720 torr, although a lower pressure, may be used. The duration of the reaction necessary to obtain the specified yield of by-product is generally from 10 to 90 minutes. The reaction is preferably carried out in the absence of water and by agitation, for example by stirring a mixture of the silane and the dialkyltin salt.

The reaction between the silane and the tin compound can be illustrated by the following equation $$R_aSi(OR^4)_{4-a} + (4-a) R^1R^2Sn(OOCR^3)_2$$

$$R_aSi(OSnR^1R^2OOCR^3)_{4-a} + (4-a) R^3COOR^4.$$

The ester formed as a by-product is removed as the reaction proceeds, and this may be conveniently done by distillation. The reaction is continued until from 80 to 100 percent of the theoretical amount of the ester formed has been removed. It can be seen from the equation that the amount of the ester theoretically formed by complete reaction is one mole per mole of the dialkyltin salt.

If desired, the silicon-tin compounds of this invention may be purified by recrystallization from an organic solvent, for example petroleum ether. In order for the compound to be crystalline at room temperature, at least 90 percent of the number of radicals represented by R, $R^1$, $R^2$ and $R^3$, respectively, must each be the same in the corresponding molecule; i.e., the radicals represented by $R^3$ may be different from those represented by R and/or $R^1$ and/or $R^2$; however, at least 90 percent of the number of radicals represented by $R^3$ should be the same in each molecule. The reaction product will not crystallize, for example when the radical represented by $R^3$ is a mixture of the isomeric pentyl radicals.

If the compound of this invention is to be used as a condensation catalyst in the preparation of an organopolysiloxane elastomer, purification of the compound, for example by recrystallization, is generally unnecessary. The compounds of this invention may also be used, for example, as stabilizers for polyvinyl chloride and as catalysts in the preparation of foamed polyurethane plastics.

The present invention also provides a method for preparing organopolysiloxane elastomers, which comprises curing a composition containing a diorganopolysiloxane having at least one condensable group or atom in the terminal units, the silicon-tin compound of this invention and, if necessary or desired, a cross-linking agent.

It was surprising to discover that the organopolysiloxane elastomers produced using the silicon-tin compounds of this invention do not suffer reversion when heated within 24 hours after their preparation. Reversion has been defined as the tendency of the elastomer to soften or become liquid, generally beginning internally of the elastomer and spreading outward. Heretofore, it was thought that, only radicals represented by $R^3$ having branched alkyl groups linked to the alpha position to the carboxyl group and having at least 7 carbon atoms could be employed to prevent reversion (see U.S. Pat. No. 3,678,002).

Diorganopolysiloxanes which may be used in the preparation of the organopolysiloxane elastomers are preferably those having the general formula $$Z_nSiR^5{}_{3-n}O(SiR^5{}_2O)_xSiR^5{}_{3-n}Z_n$$

in which $R^5$ represents a monovalent, substituted or unsubstituted monomeric or polymeric hydrocarbon radical, Z represents a hydrolyzable group or atom or a hydroxy group, n represents b 1, 2 or 3, and x represents a positive integer. Also there may be present, within or along the siloxane chain, a small amount of siloxane units other than the diorganosiloxane units, such as units of the formulae $R^5SiO_{3/2}$, $R^5{}_3SiO_{1/2}$ and $SiO_{4/2}$. Such units are generally present only as impurities and are preferably present in an amount below about 10 mole percent.

Examples of unsubstituted monomeric hydrocarbon radicals represented by $R^5$ are alkyl radicals, e.g., methyl, ethyl, propyl, butyl, hexyl and octyl radicals; Alkenyl radicals, e.g., vinyl, allyl, ethallyl and butadienyl radicals; aryl radicals, e.g., phenyl radicals; and alkaryl radicals, e.g., tolyl radicals. Examples of preferred substituted monomeric hydrocarbon radicals are halohydrocarbon radicals, e.g., 3,3,3-trifluoropropyl, chlorophenyl and bromotolyl radicals, and cyanoalkyl radicals, e.g., beta-cyanoethyl radicals. Examples of unsubstituted and substituted polymeric (or "modifying") hydrocarbon radicals are homopolymeric and copolymeric chains derived from one or more olefinically unsaturated monomers (e.g., styrene, vinyl acetate, n-butyl acrylate, n-butyl methacrylate and acrylonitrile) in which the polymeric chains are linked to the silicon atom via a carbon-carbon bond. Preferably at least 50 percent of the radicals represented by $R^5$ are methyl radicals, since these are more readily available. Any other radicals represented by $R^5$ are preferably phenyl or vinyl radicals.

Hydrolyzable groups represented by Z are, for example, amino, acylamino, aminoxy, oximo, hydrocarbonoxy, alkoxyalkoxy, acyloxy and phosphato groups. Suitable amino groups are, for example, n-butylamino, sec-butylamino and cyclohexylamino groups. An example of suitable acylamino groups is a benzoylmethylamino group. Suitable aminoxy groups are, for example, dimethylaminoxy, diethylaminoxy, dipropylaminoxy, dibutylaminoxy, dioctylaminoxy, diphenylaminoxy, ethylmethylaminoxy and methylphenylaminoxy groups. Suitable oximo groups are, for example, acetophenone oxime, acetone oxime, benzophenone oxime, methyl ethyl ketoxime, diisopropyl ketoxime and chlorocyclohexanone oxime groups. Examples of hydrocarbonoxy groups are alkoxy groups having up to 10 carbon atoms, e.g., methoxy, ethoxy, n-propoxy, isopropoxy, butoxy, hexyloxy, heptyloxy and octyloxy groups. Other hydrocarbonoxy groups having up to 10 carbon atoms are, e.g., vinyloxy, allyloxy, ethylallyloxy, isopropenyloxy, butadienyloxy and phenoxy groups. A suitable alkoxyalkoxy group is, for example, a methoxyethoxy group. Examples of preferred acyloxy groups are those having up to 18 carbon atoms, e.g., formyloxy, acetoxy, propinoxy, valeroyloxy, caproyloxy, myristyloxy and stearoyloxy groups. Suitable phosphato groups are, for example, dimethylphosphato, diethylphosphato, dibutylphosphato and diphenylphosphato methylethylphosphato, methylphenylphosphato and diphenylphosphato groups.

Hydrolyzable atoms represented by Z are, for example, hydrogen atoms and halogen atoms, e.g., chlorine atoms.

Mixtures of two or more diorganopolysiloxanes may be used in the preparation of the organopolysiloxane elastomers.

The viscosity of the diorganopolysiloxane is preferably within the range of from 100 to $10^6$ cp at 25° C.

If the diorganopolysiloxane is terminated by a hydroxysiloxy group, that is to say if Z represents a hydroxy group (in which case n usually represents 1), it is essential that a cross-linking agent be employed in the preparation of the elastomer. The crosslinking agent is preferably a silicon compound having at least three condensable atoms and/or groups per molecule.

The preferred crosslinking agent is a silane which may be represented by the general formula $$R^5_{4-t}SiZ^1_t$$

in which $R^5$ is the same as above, $Z^1$ represents a hydrolyzable atom or group, and $t$ represents 3 or 4.

The examples of hydrolyzable atoms and groups represented by Z above, are equally applicable for $Z^1$.

Suitable examples of silanes of the above formula are methyltriethoxysilane, tetraethoxysilane, methylbutoxydiethoxysilane, methyltris(methoxyethoxy)silane, methyltriacetoxysilane, isopropyltriacetoxysilane, n-propyltriacetoxysilane, isopropoxytriacetoxysilane, vinyltriacetoxysilane, methyltris(diethylaminoxy)silane, methyltris(cyclohexylamino)silane, methyltris(diethylphosphato)silane, methyltris(methyl ethyl ketoximo)silane, tetra(methoxyethoxy)silane and tetra-n-propyl silicate.

Another suitable crosslinking agent, which may be used instead of or in combination with the silane above, is a polysiloxane containing at least three silicon-bonded atoms or groups represented by $Z^1$ per molecule, in which any unsatisfied silicon valencies are satisfied by siloxane oxygen atoms or, optionally, by a radical represented by $R^5$. Examples of such crosslinking agents are polyethylsilicates having an $SiO_2$ content of about 40 percent by weight, hexaethoxydisiloxane and methylhydrogensiloxanes.

The amount of crosslinking agent employed is preferable within the range of from 0.1 to 15 percent by weight, and more preferably, from 0.5 to 5 percent by weight, based on the total weight of the composition employed in the preparation of the organopolysiloxane.

The amount of the silicon-tin compound of this invention employed as a catalyst in the preparation of the elastomer is preferably in the range of from 0.01 to 10 percent by weight and more preferably from about 0.1 to 5 percent by weight, based on the total weight of the composition.

The composition employed in the preparation of the elastomers may also contain conventional additives, such as for example, reinforcing and non-reinforcing fillers, pigments, soluble dyes, odorizers, corrosion inhibitors, plasticizers, adhesion-improving agents and solvents. Suitable fillers are, for example, pyrogenically produced silicon dioxide (fume silica), diatomaceous earths, quartz powder, aluminum silicates and polyvinyl chloride powder. Suitable plasticizers are, for example, trimethylsiloxy-terminated dimethylpolysiloxanes which are liquid at room temperature, polyglycols and etherified and/or esterified polyglycols. An agent which may be employed to improve the adhesion of the elastomer to a support on which it is applied is, for example, an epoxyalkylsilane.

The elastomers may be prepared by simply mixing the diorganopolysiloxane with the catalyst and crosslinking agent, if desired or necessary and exposing the mixture at room temperature to atmospheric moisture and pressure. Higher or lower temperatures and higher or lower pressures may be used, if desired.

The elastomers prepared in accordance with this invention may be used, for example, in the casting of electrical and electronic components and motors; in the preparation of molded articles, impressions, such as dental impressions, coatings, such as coatings on plaster molds, as insulating material as well as for sealing joints and for all other purposes in which similar elastomers have been used.

In the following examples, Examples 1 to 5 illustrate the preparation of the silicon-tin compounds of this invention, and Examples 6 to 8 illustrate their use in the preparation of organopolysiloxane elastomers. In these examples, all parts and percentages are by weight unless otherwise specified.

EXAMPLE 1

A mixture containing 351 grams (1 mole) of di-n-butyltin diacetate and 52 grams (0.25 mole) of tetraethyl silicate was heated, by means of an oil bath at 150° C, with agitation in the absence of water, in a three-necked flask equipped with a stirrer, thermometer and a countercurrent condenser (Liebig condenser). When the contents of the flask had reached a temperature of about 130° C, ethyl acetate began to condense in the condenser and was distilled off. After 15 minutes distillation at atmospheric pressure, the pressure in the flask was reduced to 10 torr and more ethyl acetate was distilled off at 80° C. A silicon-tin compound of the formula $$Si[OSn(n-C_4H_9)_2OOCH_3]_4$$

was obtained in a quantitative yield. The product was in the form of wax-like sperulites, which dissolved readily in petroleum ether, cyclohexane, ethyl acetate, dichloroethane, carbon tetrachloride, acetone, tetra(methoxyethoxy)silane, tetra-n-propyl silicate, hexaethoxydisiloxane and dioxane. About 84 grams of ethyl acetate were recovered.

50 grams of the silicon-tin compound were dissolved in 50 milliliters of petroleum ether having a boiling range of 60° to 70° C. The solution was filtered through a sintered-glass filter and cooled by means of a mixture of solid $CO_2$-methanol. About 30 grams of rod-like crystals, melting at 52°–56° C, were obtained.

| Analysis: | Calculated | Actual |
|---|---|---|
| | Sn 37.7 % | Sn 36.8 % |
| | Si 2.2 % | Si 2.0 % |

EXAMPLE 2

A mixture containing 351 grams (1 mole) of di-n-butyltin diacetate and 38 grams (0.25 mole) of tetramethyl silicate were heated by means of an oil bath at 120° C, with agitation and in the absence of water in a three-necked flask equipped with stirrer, thermometer and a descending countercurrent condenser. When the contents of the flask had reached a temperature of about 110° C, methyl acetate began to condense in the condenser and was distilled off. After 15 minutes distillation at atmospheric pressure, the pressure in the flask was reduced to 10 torr and further methyl acetate was distilled off at 60° C. The same silicon-tin compound as in Example 1 was obtained, in an almost quantative yield. About 68.5 grams of methyl acetate were also recovered.

EXAMPLE 3

The procedure of Example 1 was repeated, except that 66 grams (0.25 mole) of tetra-n-propyl silicate were substituted for 52 grams of tetraethyl silicate. The same silicon-tin compound as in Example 1 was obtained, in an almost quantative yield, and about 95.3 grams propyl acetate were also recovered.

EXAMPLE 4

A mixture containing 351 grams (1 mole) of di-n-butyltin diacetate and 59.3 grams (0.33 mole) of methyltriethoxysilane were heated, by means of an oil bath at 150° C, with agitation and in the absence of water in a three-necked flask equipped with a stirrer, thermometer and a reflux condenser. When the contents of the flask had reached a temperature of about 130° C, reflux commenced and the oil bath was no longer heated externally. About 20 minutes after the onset of refluxing, the oil bath had cooled to a temperature of 130° C and the flask contents had cooled down to 100° C. When the oil bath had cooled to a temperature of about 80° C it was maintained at this temperature and ethyl acetate was distilled off at 10 torr. A silicon-tin compound of the formula $$CH_3Si[OSn(n-C_4H_9)_2OOCCH_3]_3$$

was obtained in about 90 percent yield based on theoretical. It was in the form of translucent rods, which dissolved readily in petroleum ether. About 68.9 grams of ethyl acetate were also recovered.

EXAMPLE 5

A mixture containing 351 grams (1 mole) of di-n-butyltin diacetate and 80 grams (0.33 mole) of phenyltriethoxysilane were heated, by means of an oil bath at 150° C, with agitation and in the absence of water in a three-necked flask equipped with stirrer, thermometer and reflux condenser. When the temperature of the flask reached 131° C, the contents of the flask began to reflux. About 20 minutes after the onset of refluxing, the contents of the flask had cooled to 102° C, and the oil bath was no longer heated externally. When the oil bath had cooled to 80° C it was maintained at this temperature and ethyl acetate was distilled off at 10 torr. When no more ethyl acetate distilled off, the descending condenser was replaced by a reflux condenser and the oil bath was heated for 30 minutes at 150° C. Slight refluxing was observed when the contents of the flask had reached 131° C. When the oil bath had cooled again to 80° C, it was kept at this temperature and additional ethyl acetate was distilled off at 10 torr. A silicon-tin compound of the formula $$C_6H_5Si[OSn(n-C_4H_9)_2OOCCH_3]_3$$

was obtained in about 90 percent yield, based on theoretical. It was in the form of sperulites, which could be recrystallized in petroleum ether and were readily soluble in cyclohexane, ethyl acetate, dichloroethane, carbon tetrachloride, acetone and dioxane and had a melting point of 45° C. A total of 84.6 grams of ethyl acetate were also recovered.

EXAMPLE 6

A mixture containing 200 grams of a hydroxysiloxy-terminated dimethylpolysiloxane having a viscosity of 19,500 cp at 23° C and 100 grams of diatomaceous earth was mixed with 6 grams of a solution containing 1 part of the silicon-tin compound of the formula $Si[OSn(n-C_4H_9)_2OOCCH_3]_4$ and 5 parts of tetra(methoxyethoxy)-silane $[(CH_3OCH_2CH_2O)_4 Si]$. The resultant composition began to crosslink at room temperature and after 40 seconds it became elastic and after 100 seconds it was tack-free. After about 5 minutes, the Shore hardness A of the resulting organopolysiloxane elastomer was 40.

EXAMPLE 7

A mixture containing 200 grams of a hydroxysiloxy-terminated dimethylpolysiloxane having a viscosity of 9800 cs at 23° C and 100 grams of quartz powder was mixed with 6 grams of a solution containing 1 part of the silicon-tin compound of the formula $Si[OSn(C_4H_9)_2OOCCH_3]_4$ in 20 parts of tetra-n-propyl silicate. The resultant composition began to crosslink at room temperature and after 3 hours it became elastic and after 10 hours was tack-free. After 24 hours, the Shore hardness A of the elastomer was 30. After storing for 2 days and then after heating for 15 hours in a drying oven at 150° C, a cross section of the elastomer was examined. No internal plasticization could be detected.

EXAMPLE 8

The procedure of Example 7 was repeated except that about 20 parts of hexaethoxydisiloxane were substituted for the tetra-n-propylsilicate. The resultant composition began to crosslink at room temperature and became elastic after 24 minutes and after 65 minutes was tack-free. After 5 hours, the Shore hardness A of the resulting elastomer was 34. A sample of the elastomer which was stored and heated in accordance with Example 7, showed no signs of internal plasticization.

Although specific examples of the invention have been described herein, it is not intended to limit the invention solely thereto, but to include all the modifications falling within the spirit and scope of the appended claims.

What is claimed is:

1. An organopolysiloxane composition capable of being cured to an elastomeric solid at room temperature in atmospheric moisture comprising a hydroxyl-terminated diorganopolysiloxane, a silicon compound capable of crosslinking with the diorganopolysiloxane and from 0.01 to 10 percent by weight based on the total weight of the composition of a silicon-tin compound of the formula $$R_a Si(OSn R^1R^2OOCR^3)_{4-a}$$

which is obtained from the reaction of a silane having the formula $$R_a Si(OR^4)_{4-a}$$

with a dialkyltin salt of the formula $$R^1R^2 Sn(OOCR^3)_2$$

in a mol ratio of (4-a) mols of dialkyltin salt per mol of silane, R is selected from the group consisting of an alkyl and phenyl radical, $R^1$, $R^2$ and $R^3$ each represent an alkyl radical, $R^4$ is a monovalent hydrocarbon radical having up to 4 carbon atoms and $a$ is 0 or 1.

2. The composition of claim 1, wherein the diorganopolysiloxane is represented by the general formula $$Z_nSiR^5_{3-n}O(SiR^5_2O)_xSiR^5_{3-n}Z_n$$

in which each $R^5$ is a monovalent hydrocarbon radical selected from the class consisting of unsubstituted, substituted, monomeric and polymeric, hydrocarbon radicals, Z is a hydroxy group, $n$ is 1 and $x$ represents a positive integer.

3. The composition of claim 2, wherein at least 50 percent of the radicals represented by $R^5$ are methyl radicals.

4. The composition of claim 3, wherein any remaining radicals represented by $R^5$ are vinyl radicals.

5. The composition of claim 1, wherein the silicon compound is a silane of the general formula $$R^5_{4-t}SiZ^1_t$$

in which $R^5$ is a monovalent hydrocarbon radical selected from the class consisting of unsubstituted, substituted, monomeric and polymeric, hydrocarbon radicals, $Z^1$ is selected from the group consisting of amino, acylamino, aminoxy, oxime, hydrocarbonoxy, alkoxyalkoxy, acyloxy and phosphato groups and $t$ is 3 or 4.

6. The composition of claim 1, wherein the silicon compound is a polysiloxane containing at least three silicon-bonded hydrolyzable groups selected from the group consisting of amino, acylamino, aminoxy, oxime, hydrocarbonoxy, alkoxyalkoxy, acyloxy and phosphato groups and any unsatisfied silicon valences are satisfied by a group selected from the class consisting of siloxane oxygen atoms and a radical represented by $R^5$ in which $R^5$ is a monovalent hydrocarbon radical selected from the class consisting of unsubstituted, substituted, monomeric and polymeric, hydrocarbon radicals.

7. The composition of claim 1, wherein the silicon compound is present in an amount of from 0.1 to 15 percent by weight, based on the total weight of the composition.

8. An improved process for curing an organopolysiloxane composition containing a hydroxyl-terminated diorganopolysiloxane, and a silicon compound capable of crosslinking with the diorganopolysiloxane at room temperature in the presence of atmospheric moisture to form an elastomeric solid, the improvement which comprises adding to said composition from 0.01 to 10 percent by weight based on the total weight of the composition of a silicon-tin compound of the formula $$R_a Si(OSn\ R^1R^2OOCR^3)_{4-a}$$

which is obtained from the reaction of a silane having the formula $$R_a Si(OR^4)_{4-a}$$

with a dialkyltin salt of the formula $$R^1R^2 Sn(OOCR^3)_2$$

in a mol ratio of (4-a) mols of dialkyltin salt per mol of silane, R is selected from the group consisting of an alkyl and phenyl radical, $R^1$, $R^2$ and $R^3$ each represent an alkyl radical, $R^4$ is a monovalent hydrocarbon radical having up to 4 carbon atoms and $a$ is 0 or 1.

* * * * *